US 7,625,548 B2

(12) United States Patent
Nguyen et al.

(10) Patent No.: US 7,625,548 B2
(45) Date of Patent: Dec. 1, 2009

(54) METHODS AND APPARATUS FOR PRODUCING NANOSCALE PARTICLES

(75) Inventors: Tung T. Nguyen, Midlothian, VA (US); Nina Brown, Sterling, VA (US); Jui C. Lin, Fairfield, CA (US); Stephen Pham, Chesterfield, VA (US); Kenneth A. Cox, Powhatan, VA (US); Douglas D. McRae, Chesterfield, VA (US); Walter A. Nichols, Chesterfield, VA (US)

(73) Assignee: Philip Morris USA Inc., Richmond, VA (US)

( * ) Notice: Subject to any disclaimer, the term of this patent is extended or adjusted under 35 U.S.C. 154(b) by 87 days.

(21) Appl. No.: 12/149,604

(22) Filed: May 5, 2008

(65) Prior Publication Data

US 2008/0268060 A1    Oct. 30, 2008

Related U.S. Application Data

(63) Continuation of application No. 10/866,194, filed on Jun. 14, 2004, now abandoned.

(60) Provisional application No. 60/477,915, filed on Jun. 13, 2003, provisional application No. 60/517,999, filed on Nov. 7, 2003.

(51) Int. Cl.
*A61K 47/06* (2006.01)
(52) U.S. Cl. .......................... 424/1.13; 75/370; 424/40; 424/489; 516/6
(58) Field of Classification Search ............... 424/1.13, 424/40, 489; 516/6; 75/370
See application file for complete search history.

(56) References Cited

U.S. PATENT DOCUMENTS

| 4,572,007 A | 2/1986 | Postma |
| 4,963,289 A | 10/1990 | Ortiz et al. |
| 4,977,785 A | 12/1990 | Willoughby et al. |
| 5,175,433 A | 12/1992 | Browner et al. |
| 5,247,842 A | 9/1993 | Kaufman et al. |
| 5,743,251 A | 4/1998 | Howell et al. |

(Continued)

OTHER PUBLICATIONS

Gomez et al., "Production of Protein Nanoparticles by Electrospray Drying", *J. Aerosol Sci.*, vol. 29, No. 5/6 pp. 561-574 (1998) Elsevier Science Ltd.

*Primary Examiner*—H. (Holly) T Le
(74) *Attorney, Agent, or Firm*—Buchanan Ingersoll & Rooney PC

(57) ABSTRACT

Liquid nanoscale particle precursor materials for generating nanoscale particles include at least one high volatility carrier and a second component. A nanoscale particle generating device generates nanoscale particles by passing a liquid nanoscale particle precursor material through a flow passage heated to convert the carrier into a vapor and the second component into nanoscale particles. The nanoscale particles preferably consist essentially of the second component and can consist essentially of dry, solid particles. The particle generator can be incorporated in a hand held inhaler, and can be delivered to a targeted portion of the lung using the inhaler. Composite controlled release particles of micron or nanoscale size can be produced by flowing a solution of medicament, control release agent and carrier liquid through a capillary heater.

56 Claims, 10 Drawing Sheets

U.S. PATENT DOCUMENTS

| | | |
|---|---|---|
| 5,874,064 A * | 2/1999 | Edwards et al. ............... 424/46 |
| 5,914,122 A | 6/1999 | Otterbeck et al. |
| 5,932,249 A | 8/1999 | Gruber et al. |
| 5,958,361 A | 9/1999 | Laine et al. |
| 6,051,257 A | 4/2000 | Kodas et al. |
| 6,096,118 A | 8/2000 | Altman |
| 6,119,953 A | 9/2000 | Gañán-Calvo et al. |
| 6,165,247 A | 12/2000 | Kodas et al. |
| 6,234,167 B1 | 5/2001 | Cox et al. |
| 6,491,233 B2 | 12/2002 | Nichols |
| 6,501,052 B2 | 12/2002 | Cox et al. |
| 6,516,796 B1 | 2/2003 | Cox et al. |
| 6,557,552 B1 | 5/2003 | Cox et al. |
| 6,568,390 B2 | 5/2003 | Nichols et al. |
| 6,640,050 B2 | 10/2003 | Nichols et al. |
| 6,799,572 B2 | 10/2004 | Nichols et al. |
| 6,883,516 B2 * | 4/2005 | Hindle et al. .......... 128/200.14 |
| 7,425,582 B2 * | 9/2008 | Baran et al. ................. 424/489 |
| 7,501,113 B2 * | 3/2009 | Blondino et al. ............... 424/45 |
| 7,521,068 B2 * | 4/2009 | Bosch et al. ................. 424/489 |
| 7,581,540 B2 * | 9/2009 | Hale et al. ............. 128/203.27 |
| 2002/0033173 A1 | 3/2002 | Shofner, II et al. |
| 2002/0078948 A1 | 6/2002 | Hindle et al. |
| 2003/0013606 A1 | 1/2003 | Hampden-Smith et al. |
| 2003/0033055 A1 | 2/2003 | McRae et al. |

* cited by examiner

METHODS AND APPARATUS FOR PRODUCING NANOSCALE PARTICLES

CROSS-REFERENCE TO RELATED APPLICATIONS

This application is a continuation of prior application Ser. No. 10/866,194, filed Jun. 14, 2004, now abandoned which claims the benefit of U.S. Provisional Application No. 60/477,915, filed on Jun. 13, 2003 and U.S. Provisional Application No. 60/517,999, filed on Nov. 7, 2003; the entire contents of each of which are hereby incorporated by reference.

BACKGROUND

Provided are compositions of matter, apparatus and methods that relate generally to the generation of nanoscale particles. More specifically, provided are nanoscale particle precursor materials, nanoscale particle generating devices and methods for generating nanoscale particles using a capillary aerosol generator.

Aerosol generators are known that include a heated tube for vaporizing liquid. For example, commonly-assigned U.S. Pat. No. 5,743,251, which is incorporated herein by reference in its entirety, discloses an aerosol generator including a tube and a heater operable to heat the tube to a sufficient temperature to volatilize liquid in the tube. An aerosol is formed as volatilized material expands out an open end of the tube and admixes with ambient air.

Methods and apparatus for generating an aerosol are disclosed in U.S. Pat. Nos. 5,175,433 and 4,977,785 and in co-pending U.S. application Ser. No. 09/966,562, filed Sep. 26, 2001. Methods for generating ultra-fine particles are disclosed by Gomez et al. in *J. Aerosol Sci.*, Vol. 29, No. 5/6, pp. 561-574 (1998); in U.S. Pat. Nos. 5,958,361 and 5,247,842, and in co-pending U.S. application Ser. No. 10/210,600, filed Aug. 1, 2002.

Aerosol generators including a heated capillary for vaporizing liquids to produce an aerosol are described in commonly-assigned U.S. Pat. Nos. 6,640,050; 6,568,390; 6,557,552; 6,516,796; 6,501,052; 6,491,233 and 6,234,167, and in co-pending and commonly assigned U.S. application Ser. No. 10/206,320, filed Jul. 29, 2002; U.S. Ser. No. 09/981,739, filed Oct. 19, 2001, each incorporated herein by reference in its entirety.

SUMMARY

Precursor materials for producing nanoscale particles are provided. In addition, nanoscale particle generating devices and methods for, generating and capturing nanoscale particles are provided.

An embodiment of a liquid nanoscale particle precursor material for producing nanoscale particles via aerosolization comprises a high volatility liquid carrier and a second component. In preferred embodiments, the liquid carrier can be heated to form a vapor that does not form an appreciable condensation aerosol when the vapor is admixed with cooler air. The second component, however, forms an aerosol of nanoscale particles when the liquid carrier is volatilized. Thus, by heating the liquid nanoscale particle precursor material, the particles that form comprise substantially dry particles of only the second component. Preferred second components are medicaments such as albuterol or budesonide.

In a further preferred embodiment, the liquid nanoscale particle precursor material is propellant free. Further, the liquid nanoscale particle precursor material is preferably a solution. In such preferred embodiments, the second component is a solute, which is dissolved in the high volatility liquid carrier. The high volatility carrier, which can comprise ethanol, a mixture of ethanol and water, acetone or ethyl acetate, preferably has a boiling point of 100° C. or less.

An embodiment of a nanoscale particle generating device for generating nanoscale particles via aerosolization comprises a liquid source and a flow passage in fluid communication with the liquid source. The liquid source contains a liquid nanoscale particle precursor material including a high volatility carrier and a second component. A heater is disposed to heat liquid in the flow passage to vaporize the high volatility carrier. Nanoscale particles of the second component exit an outlet end of the flow passage and are admixed with air. In a preferred embodiment, the nanoscale particles comprise substantially only the second component.

The nanoscale particles can be collected directly from the aerosol stream using filtration, condensation or diffusional capture. According to a preferred embodiment, a liquid suspension of the nanoscale particles is formed directly from the aerosol stream.

DETAILED DESCRIPTION OF PREFERRED EMBODIMENTS

Figure 1:
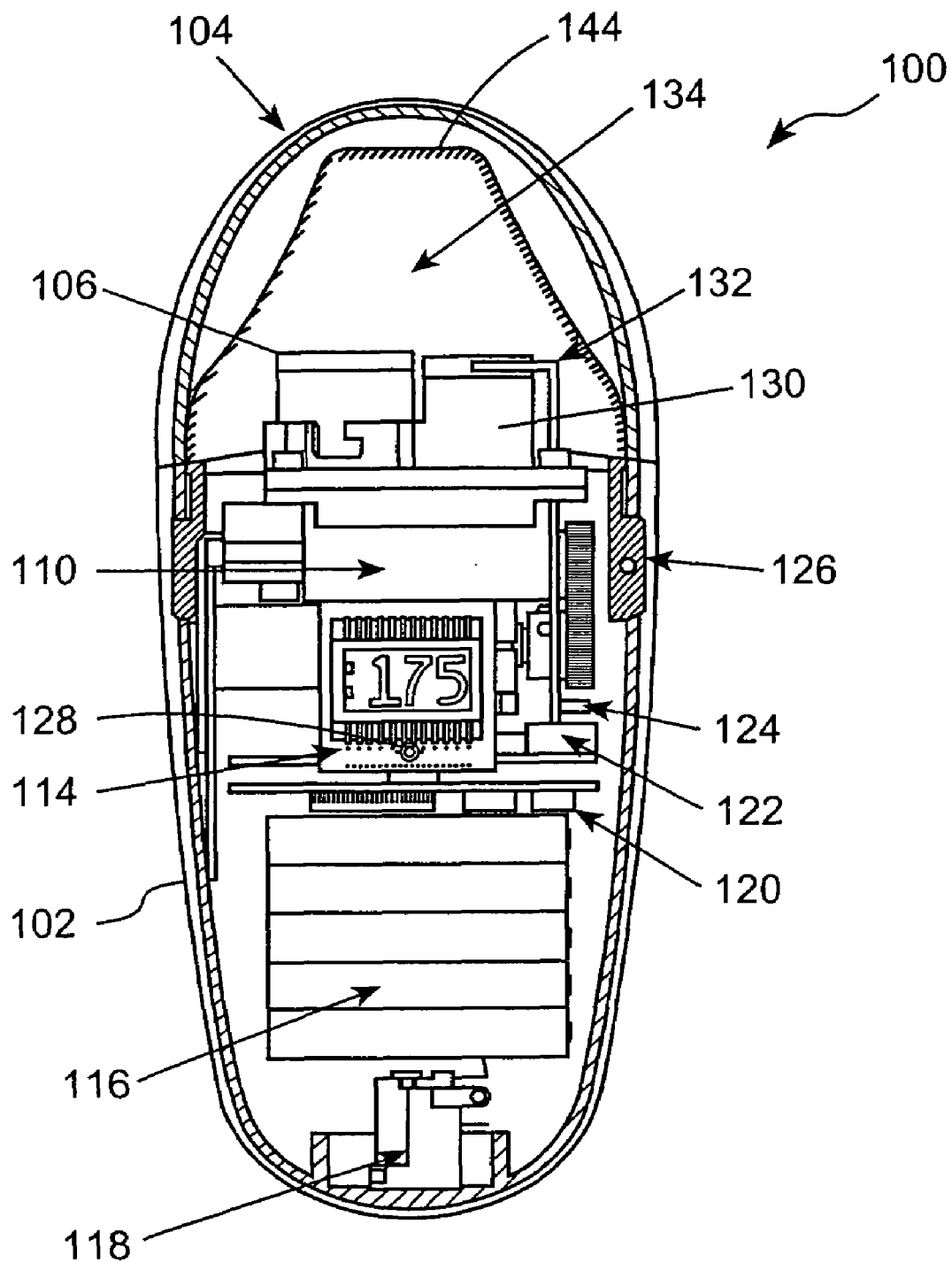
FIG. 1 illustrates an embodiment of a nanoscale particle generating device.

Liquid nanoscale particle precursor materials, nanoscale particle generating devices and methods for generating nanoscale particles from the nanoscale particle precursor materials are provided.

The liquid nanoscale particle precursor materials can produce nanoscale particles having selected compositions and controlled particle sizes. The liquid nanoscale particle precursor materials are suitable for different applications. For example, for drug delivery applications via inhalation, the liquid nanoscale particle precursor materials can be used to produce nanoscale particles having a desirable mass median aerodynamic diameter for targeted delivery.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD. For pulmonary delivery, particles of smaller size are desired than for tracheobronchial delivery or delivery to the oropharynx or mouth. In preferred embodiments, the liquid nanoscale particle precursor materials can be used to produce particles having a controlled particle size that is effective to achieve pulmonary delivery of drug formulations.

In other applications, the liquid nanoscale particle precursor materials can be used to produce bulk quantities of nanoscale particles. Exemplary industrial applications include producing dry nanoscale particles for coatings, and producing particles of solid materials (e.g., metals, metal oxides and/or alloys) for various uses including micro ball bearings, foam metals and microelectronic applications. For example, magnetic nanoscale metal particles of cobalt or nickel, or nanoscale alloy particles having a ferritic structure can be used in high density magnetic recording media, in magnetic bio-separation, in radar-absorbing composites and in RF/microwave components. Semiconductor nanoscale particles, such as nanoscale bismuth or silicon particles, can be used in elements of thermo-electric devices, in luminescent tags and optoelectronic components and in magneto-optical materials. Nanoscale particles can also be used in abrasive media for fine polishing and as components of fertilizers or lubricants. The mass median aerodynamic diameter of the nanoscale particles is preferably less than about 500 nm. Preferably, the particles have a mass median aerodynamic diameter between 10 nm and 500 nm, 10 nm and 400 nm, 10 nm and 300 nm, 10 nm and 200 nm, or 10 nm and 100 nm.

The liquid nanoscale particle precursor materials include at least one high volatility carrier and at least one second component. In a preferred embodiment, the carrier is a liquid and the second component is a solute dissolved in the carrier. However, the liquid nanoscale particle precursor material can alternatively be a suspension of the second component in the high volatility carrier(s). In other embodiments, the liquid nanoscale particle precursor material can be a dispersion, gel or an emulsion.

As used herein, the term "high volatility carrier" denotes a liquid that has a boiling point higher than 25° C. and remains substantially in the vapor state when it is vaporized by heating and the resulting vapor is admixed with ambient air. However, the second component of the liquid nanoscale particle precursor material forms an aerosol of nanoscale particles when the liquid nanoscale particle precursor material is vaporized and admixed with ambient air. By combining at least one high volatility carrier and second component, the liquid nanoscale particle precursor materials can be used to produce liquid or solid nanoscale particles that are substantially particles of only the second component, i.e., nanoscale particles that are substantially free of the high volatility carrier.

The high volatility carriers have a low boiling point. In a preferred embodiment, the high volatility carriers have a boiling point of 100° C. or less, where 100° C. is the boiling point of water at atmospheric pressure. A preferred high volatility carrier is ethyl alcohol (ethanol), which has a boiling point of about 78° C. at a pressure of 1 atmosphere. Ethanol can be used in combination with other liquids, e.g., ethanol/water solutions. For example, the liquid nanoscale particle precursor material can contain as the high volatility carrier 100% ethanol, 100% water, and mixtures thereof.

Ethanol and other suitable high volatility carriers can be used as solvents for liquid nanoscale particle precursor materials, such as drug formulations, which form an aerosol comprising nanoscale particles when heated into a vapor state and the vapor is admixed with air in which the carrier is present substantially only in the vapor state, i.e., substantially no aerosol of the carrier is formed. Accordingly, the particles in such aerosols are substantially only particles of the second component. When the liquid nanoscale particle precursor material is a solution and the second component is a solute, in a preferred embodiment, the particles comprise substantially only the second component. Ethanol is converted from a liquid to a vapor by heating the liquid nanoscale particle precursor material to a sufficiently high temperature. In a preferred embodiment, the concentration of ethanol in the aerosol produced from the liquid nanoscale particle precursor material is below the saturation limit of ethanol in air with which the ethanol is admixed so that ethanol vapor substantially does not convert to an aerosol. Consequently, ethanol remains substantially in the vapor phase when used to form nanoscale particles for delivery via inhalation or when used to form bulk volumes of dry nanoscale particles.

As described above, liquids other than ethanol that have a high volatility can be used as a carrier in the liquid nanoscale particle precursor materials. In a preferred embodiment, a liquid carrier that has a high volatility, but is not an FDA accepted excipient in drugs administered via inhalation, can be used in the liquid nanoscale particle precursor materials for applications other than delivering drugs via inhalation. Such other high volatility (i.e., non-condensing) liquids can include, but are not limited to, water, acetone, ethyl acetate, hexanes, other alcohols, such as isopropanol, butanol and mixtures thereof. These liquids can be used as a carrier in the liquid nanoscale particle precursor material to produce nanoscale particles that are substantially particles of only the second component(s) of the liquid nanoscale particle precursor material. Thus, the nanoscale particle can be solid particles of one or more components. The nanoscale particles can be liquid or solid particles or, if more than a single second component is used, the nanoscale particles may comprise liquid and/or solid phases.

A liquid nanoscale particle precursor material can comprise a high volatility carrier, a medicament and a third component capable of modifying the action of the medicament. According to an embodiment, the third component can be selected from the group consisting of trehalose, sucrose, cyclodextrin, manitol and lactose. According to a further embodiment, the third component can be a biodegradable polymer selected from the group consisting of polyglycolic acid (PGA), polylactic acid (PLA), polyhydroxybutyrate (PHB), polyhydroxyvalerate (PHV), polycaprolactone, polyorthoesters, polycyanocrylates and polyanhydrides.

Other applications of the liquid nanoscale particle precursor materials include those in which dry nanoscale particles are desirable. For example, the liquid nanoscale particle precursor materials can be used to produce dry, solid nanoscale particles for various industrial applications, such as particulate components for use in polishing media or for the deposition of thin film coatings.

Various substances can be used as the second component in the liquid nanoscale particle precursor materials, depending on the desired application of the liquid nanoscale particle precursor material. For example, the second component can be any suitable medicament that can be delivered to a patient as nanoscale particles (e.g., inhalation of a nanoscale aerosol or consumption of a capsule containing nanoscale particles). Exemplary suitable medicaments include, but are not limited to, one of the following classes: antibiotics, anticonvulsants, antidepressants, antiemetics, antihistamines, antiparkinsonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesic and stimulants.

Typically, where the medicament is an antibiotic, it is selected from one of the following compounds: cefinetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; lipopeptides; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

Typically, where the medicament is an anticonvulsant, it is selected from one of the following compounds: benzodiazepine, gabapentin, tiagabine, and vigabatrin.

Typically, where the medicament is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenylhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, venlafaxine, and zalospirone.

Typically, where the medicament is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron methanesulfonate, droperidol, granisetron, hyoscine, lorazepam, metoclopramide, metopimazine, ondansetron, perphenazine, promethazine, prochlorperazine, scopolamine, triethylperazine, trifluoperazine, trifluopromazine, trimethobenzamide, tropisetron, domperidone, and palonosetron.

Typically, where the medicament is an antihistamine, it is selected from one of the following compounds: azatadine, brompheniramine, chlorpheniramine, clemastine, cyproheptadine, dexmedetomidine, diphenhydramine, doxylamine, hydroxyzine, cetirizine, fexofenadine, loratidine, and promethazine.

Typically, where the medicament is an antiparkinsonian drug, it is selected one of the following compounds: amantadine, baclofen, biperiden, benztropine, orphenadrine, procyclidine, trihexyphenidyl, levodopa, carbidopa, selegiline, deprenyl, andropinirole, apomorphine, benserazide, bromocriptine, budipine, cabergoline, dihydroergokryptine, eliprodil, eptastigmine, ergoline pramipexole, galanthamine, lazabemide, lisuride, mazindol, memantine, mofegiline, pergolike, pramipexole, propentofylline, rasagiline, remacemide, spheramine, terguride, entacapone, and tolcapone.

Typically, where the medicament is an antipsychotic, it is selected from one of the following compounds: acetophenazine, alizapride, amperozide, benperidol, benzquinamide, bromperidol, buramate, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, trifluopromazine, trifluoperazine, ziprasidone, zotepine, zuclopenthixol, amisulpride, butaclamol, clozapine, melperone, olanzapine, quetiapene, and risperidone.

Typically, where the medicament is a drug that is an anxiolytic, it is selected from one of the following compounds: mecloqualone, medetomidine, metomidate, adinazolam, chlordiazepoxide, clobenzepam, flurazepam, lorazepam, loprazolam, midazolam, alpidem, alseroxion, amphenidone, azacyclonol, bromisovalum, buspirone, calcium N-carboamoylaspartate, captodiamine, capuride, carbocloral, carbromal, chloral betaine, enciprazine, flesinoxan, ipsapirone, lesopitron, loxapine, methaqualone, methprylon, propanolol, tandospirone, trazadone, zopiclone, and zolpidem. Nanoscale particles can be formed from sedative-hypnotics such as zaleplom, zopiclone, and zolpidem.

Typically, where the medicament is a drug for erectile dysfunction, it is selected from one of the following compounds: cialis (IC351), sildenafil, vardenafil, apomorphine, apomorphine diacetate, phentolamine, and yohimbine. Medicament nanoscale particles for treating sexual dysfunction in a female individual, comprising administering to the vagina, vulvar area or urethra of the individual a pharmaceutical formulation that comprises an effective amount of a vasoactive agent selected from the group consisting of naturally occurring prostaglandins, synthetic prostaglandin derivatives, endothelial-derived relaxation factors, vasoactive intestinal polypeptide agonists, smooth muscle relaxants, leukotriene inhibitors, calcium channel blockers, phosphodiesterase inhibitors, nitrates, α-receptor blocking agents, ergotamine drugs, antihypertensive agents, pharmacologically acceptable salts, esters, analogs, derivatives, prodrugs and inclusion complexes of any of the foregoing, and combinations thereof.

Typically, where the medicament is a drug for migraine headache, it is selected from one of the following compounds: ahnotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the medicament is a drug for the treatment of alcoholism, it is selected from one of the following compounds: naloxone, naltrexone, and disulfiram.

Typically, where the medicament is a drug for the treatment of addiction it is buprenorphine.

Typically, where the medicament is a muscle relaxant, it is selected from one of the following compounds: baclofen, cyclobenzaprine, orphenadrine, quinine, and tizanidine.

Typically, where the medicament is a nonsteroidal anti-inflammatory, it is selected from one of the following compounds: aceclofenac, alminoprofen, amfenac, aminopropylon, amixetrine, benoxaprofen, bromfenac, bufexamac, carprofen, choline, salicylate, cinchophen, cinmetacin, clopriac, clometacin, diclofenac, etodolac, indoprofen, mazipredone, meclofenamate, piroxicam, pirprofen, and tolfenamate.

Typically, where the medicament is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Typically, where the medicament is another analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the medicament is a stimulant, it is selected from one of the following compounds: amphetamine, brucine, caffeine, dexfenfluramine, dextroamphetamine, ephedrine, fenfluramine, mazindol, methylphenidate, pemoline, phentermine, and sibutramine.

If desired, medicament nanoscale particles can be formed from esters of antibiotics; esters of anticonvulsants; esters of antidepressants; esters of antihistamines; esters of antiparkinsonian drugs; esters of drugs for migraine headaches; esters of drugs for the treatment of alcoholism; esters of muscle relaxants; esters of anxiolytics; esters of nonsteroidal anti-inflammatories; esters of other analgesics; and, esters of steroids.

Medicament nanoscale particles can comprise physiologically active compounds comprising chlordiazepoxide, betahistine, clonidine, testosterone, conjugated estrogens, estrogen esters, estradiol, estradiol esters, ethinyl estradiol, ethinyl estradiol esters, or hyoscyamine.

Medicament nanoscale particles for treating anxiety can comprise alprazolam, estazolam, midazolam and triazolam.

Medicament nanoscale particles can be generated for treating stroke, promoting angiogenesis, promoting collateral blood vessel formation, promoting nerve regeneration, promoting wound healing, treating or preventing a nervous system disease, i.e., a central nervous system disease or a peripheral nervous system disease, or preventing myocardial damage in heart disease and surgery.

Medicament nanoscale particles can comprise beta-blockers comprising atenolol, pindolol, esmolol, propanolol or metoprolol. Medicament nanoscale particles can comprise antibacterial agents comprising lipopeptide compounds.

Medicament nanoscale particles can comprise polysaccharides such as glycosaminoglycan, a heparin, a heparin sulfate, a low molecular weight heparin, a biotechnology derived heparin, a chemically modified heparin, a heparin mimetic (e.g., a monosaccharide, oligosaccharide or polysaccharide that has at least one heparin-like function such as AT-III binding), or an unfractionated heparin preparation.

In preferred embodiments, the medicament in the liquid nanoscale particle precursor material is albuterol or budesonide, which are used for the treatment of asthma. Both albuterol and budesonide are sufficiently soluble in ethanol to form solutions at ambient conditions. Ethanol solutions of albuterol and budesonide can be provided in different compositions. For example, a solution of a medicament (e.g., albuterol and budesonide) in ethanol can be used to produce aerosols for delivering a therapeutically effective dose of the medicament via inhalation. The concentration of the medicament in the solution can be varied to control the amount of the medicament in such aerosols. According to an embodiment, a solution of a medicament in ethanol can be used to produce dry nanoscale particles of the medicament. A bulk volume of dry nanoscale particles of the medicament can be incorporated in various drug delivery formulations (e.g., capsules for oral administration, liquids for injection or ointments for topical administration).

Solutions can also be formed using a carrier including ethanol and water. For example, ethanol and water/albuterol solutions can be formed. In addition, water/albuterol solutions can be formed.

Other exemplary substances that can be used in the liquid nanoscale particle precursor materials to produce nanoscale particles for delivery via inhalation and/or to produce bulk dry nanoscale particles, include other active pharmaceutical ingredients such as buspirone, buprenorphine, triazolam, cyclobenzaprene, zolpidem, morphine, butalbital and caffeine.

The liquid nanoscale particle precursor material does not have to include a medicament. For example, the liquid nanoscale particle precursor material may include another type of substance, such as components for use in paints, abrasives or scents.

As mentioned above, the at least one high volatility carrier and second component can alternatively be provided in a suspension comprising solid particles in a liquid, i.e., solid particles of the second component in the high volatility liquid carrier. As with the above-described solutions, such suspensions can be heated to form liquid and/or solid nanoscale particles that are substantially particles of only the second component.

In embodiments in which the liquid nanoscale particle precursor materials are used to form nanoscale particles for other purposes, such as industrial applications, different second components can be used in the liquid nanoscale particle precursor materials depending on the desired composition of the particles. If desired, more than one second component may be used in the liquid nanoscale particle precursor material.

In a preferred embodiment, the liquid nanoscale particle precursor material is flowed through a capillary sized flow passage in which the liquid is heated to a sufficiently high temperature to vaporize the liquid. Preferably the flow passage is heated to a temperature sufficient to create nanoscale particles. By way of non-limiting example, the flow passage can be heated to a temperature of at least twice, more preferably at least 3.5 times, the boiling point of the high volatility carrier. The vaporized carrier and second component exit the flow passage as a low velocity stream of nanoscale particles, which preferably are substantially particles of the second component that admixes with gas, typically ambient air. The particles can be inhaled by a user. The size of the particles thus produced can be controlled for delivery to the lung.

Compared to propellant-assisted aerosol generators, which produce a high velocity ballistic stream, the low velocity jet that emerges from an open end of a heated capillary passage can deliver a medicated dose of nanoscale particles over a longer time, e.g., greater than 1 second, more preferably at least 2 seconds, which permits greater coordination between the formation and inhalation of the nanoscale particles in embodiments where the particles comprises a medicated dose for inhalation by a user.

FIG. 1 illustrates an exemplary embodiment of a nanoscale particle generating device 100 that can be used to produce nanoscale particles. The nanoscale particle generating device 100 includes a housing 102; a removable protective cap 104, which may activate a master on/off switch, (not shown); a fluid delivery assembly 110 including a liquid source 106 and a heater unit 130; a display 114; a battery unit 116; a charging jack 118; control electronics 120; a pressure sensor 122; an air inlet 124; a release 126 for detaching the fluid delivery assembly 110 from the nanoscale particle generating device 100; a manually actuated master activation switch 128; an air passage 132 and a removable mouthpiece 134.

In a preferred embodiment, the fluid delivery assembly 110 is removably attachable to a portion of the nanoscale particle generating device 100 by any suitable attachment construction. For example, conductive contacts (not shown) can be provided in the nanoscale particle generating device to make electrical contact with the heater unit 130, when the fluid delivery assembly 110 is attached to the device. In such embodiments, the fluid delivery assembly 110, which includes the wetted components of the device, can be replaced in the device as a complete unit. As described below, the fluid delivery assembly 110 can provide nanoscale particles having a controlled particle size. Different fluid delivery assemblies 110 that can provide nanoscale particles having different compositions and/or particle sizes can be interchanged in the device. If desired, the device can include a replaceable fluid source.

The fluid delivery assembly 110 can be replaced after liquid contained in the liquid source 106 has been consumed. A fluid delivery assembly 110 including a liquid source containing the same or a different precursor material, and that produces the same or a different particle size, can then be installed in the device.

Figure 2:
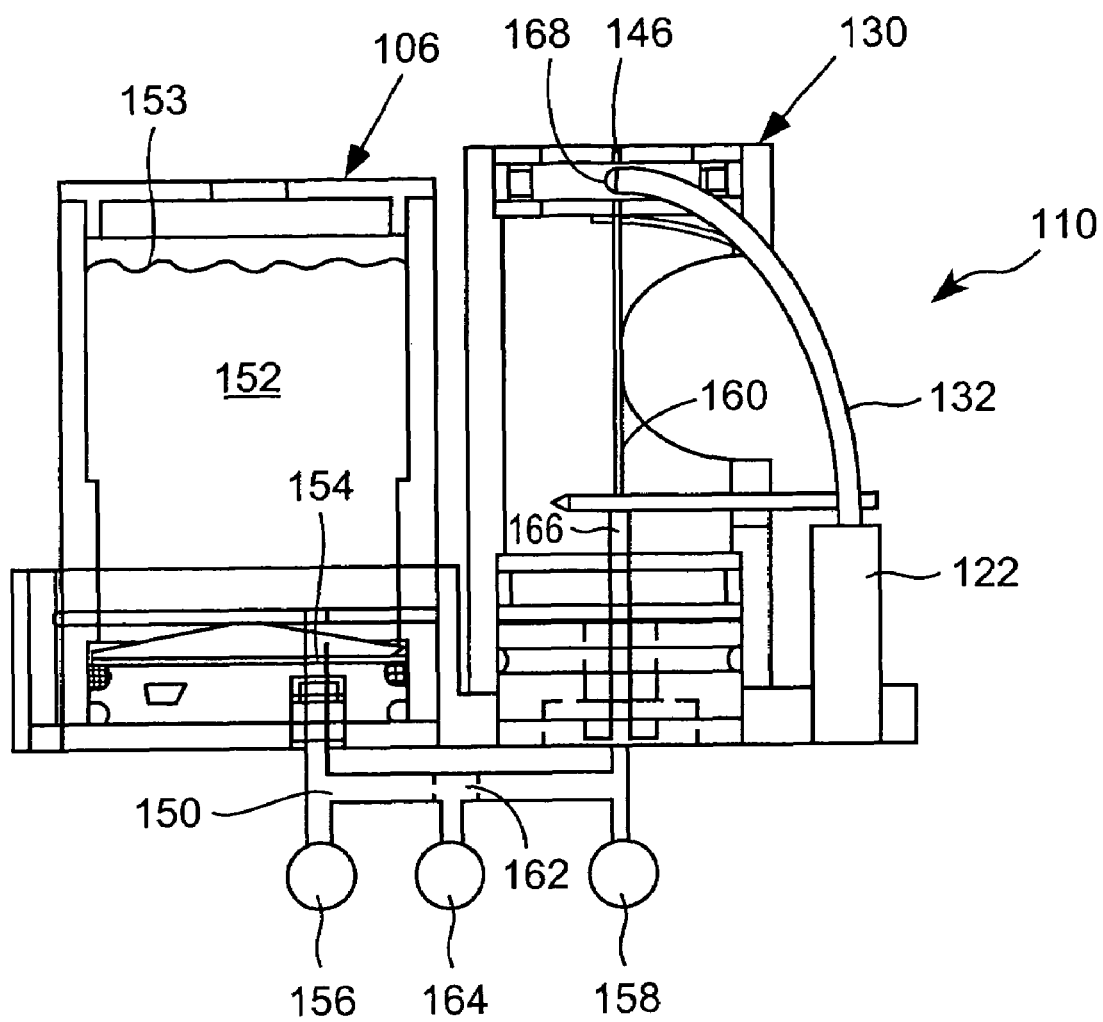
FIG. 2 illustrates an embodiment of the fluid delivery assembly of the nanoscale particle generating device.

FIG. 2 illustrates a portion of the fluid delivery assembly 110, including a liquid source 106 and heater unit 130. Liquid is supplied from the liquid source 106 to the heater unit 130 through a flow passage 150.

The liquid source 106 comprises a reservoir 152 for containing a volume of liquid 153. In an embodiment, the liquid source 106 has a liquid capacity for delivering a selected number of doses of a selected volume. For example, the doses can be 5 µL doses and the reservoir 152 can be sized to contain multiple doses. Preferably, the liquid source can contain from about 10 doses to about 500 doses, e.g., 50 to 250 doses. However, the liquid source can comprise other arrangements such as a multi-dose component wherein each dose is packaged in a separate reservoir. The liquid source can also be arranged to provide a continuous flow of the liquid in order to produce a continuous stream of nanoscale particles.

The liquid contained in the liquid source can be any liquid nanoscale particle precursor material that can be vaporized and aerosolized in the nanoscale particle generating device to produce the desired nanoscale particles. In a preferred embodiment, the liquid contains a medicament formulated to be inhaled into the user's lungs in aerosol form. The nanoscale particles can provide upper respiratory and/or deep lung delivery of a medicament to a user's lungs.

The liquid source 106 includes an upstream flow passage 154, which provides fluid communication from the reservoir 152 to the flow passage 150. The nanoscale particle generating device 100 includes at least one valve disposed to control flow of the liquid from the liquid source 106 into the heater unit 130. For instance, the nanoscale particle generating device may include a single valve (not shown) to control flow of the liquid in the flow passage, or a plurality of valves. In a preferred embodiment, the device includes an inlet valve 156 and an outlet valve 158. The inlet valve 156 is operable to open and close an inlet of the flow passage 150, which controls the supply of liquid from the liquid source 106 into the flow passage 150. The outlet valve 158 is operable to open and close an outlet end of the flow passage 150, which controls the supply of liquid from the flow passage 150 into a heated flow passage 160.

The nanoscale generating device 100 optionally includes a metering chamber 162 located in the flow passage 150 between the inlet valve 156 and the outlet valve 158. The metering chamber 162 is preferably sized to contain a predetermined volume of the liquid, such as a volume of the liquid that corresponds to one dose of the aerosolized medicament. A discharge member 164 can be used to open the metering chamber 162 during a liquid filling cycle, and to empty the metering chamber during a liquid delivery cycle, as described in greater detail below.

The heater unit 130 of the fluid delivery assembly 110 comprises a heated flow passage 160. The heated flow passage 160 is preferably a capillary sized flow passage, referred to hereinafter as a "capillary passage." The capillary passage 160 includes an open inlet end 166, and an opposite open outlet end 168. During operation of the nanoscale particle generating device 100, liquid is supplied into the capillary passage 160 at the inlet end 166 from the flow passage 150.

The capillary passage 160 can have a uniform or non-uniform transverse cross-sectional shape such as round, oval, polygonal, etc. If desired, different portions of the capillary passage can have different cross-sectional shapes. As described below, the size of the capillary passage 160 can be defined by its transverse cross-sectional area. For example, the capillary passage can have a maximum transverse dimension of 0.01 to 10 mm, preferably 0.05 to 1 mm, and more preferably 0.1 to 0.5 mm. Alternatively, the capillary passage can be defined by its transverse cross sectional area, which can be $8 \times 10^{-5}$ to 80 mm$^2$, preferably $2 \times 10^{-3}$ to $8 \times 10^{-1}$ mm$^2$, and more preferably $8 \times 10^{-3}$ to $2 \times 10^{-1}$ mm$^2$.

As an example, the heater arrangement can comprise a stainless steel tube having electrical leads attached thereto for passage of a DC current through the tube. The stainless steel tube can have any desired diameter. A 32 gauge needle has an internal diameter of 0.11 mm (0.004 inch) and a 26 gauge needle has an internal diameter of 0.26 mm (0.01 inch). If a higher flow rate of liquid is desired, a larger sized flow passage can be used to volatilize the liquid. Although a stainless steel tube can be used as a combination heater/flow passage, other arrangements can be used for the flow passage/heater arrangement. For instance, a ceramic layer can be etched to provide a groove which defines the flow passage and the ceramic layer can be overlaid with another ceramic layer which incorporates a heater such as a platinum heater arranged to heat liquid in the groove. Like the stainless steel tube, the resistance heater can be heated by passing DC current therethrough.

The material forming the capillary passage can be any suitable material, including metals, plastics, polymers, ceramics, glasses, or combinations of these materials. Preferably, the material is a heat-resistant material capable of withstanding the temperatures and pressures generated in the capillary passage, and also resisting the repeated heating cycles utilized to generate multiple doses of aerosols. In addition, the material forming the capillary passage preferably is non-reactive with the liquid that is aerosolized.

In another alternative embodiment, the capillary passage can be formed in a polymer, glass, metal and/or ceramic monolithic or multilayer (laminated) structure (not shown). Suitable ceramic materials for forming the capillary passage include, but are not limited to, alumina, zirconia, silica, aluminum silicate, titania, yttria-stabilized zirconia, or mixtures thereof. A capillary passage can be formed in the monolithic or multilayer body by any suitable technique, including, for example, machining, molding, extrusion, or the like.

In an embodiment, the capillary passage can have a length from 0.5 to 10 cm, and preferably from 1 to 4 cm.

The device can be programmed to achieve various control schemes. For instance, a resistance control scheme can be used to minimize overheating and under heating of the heater arrangement. In particular, a program can be used to send power to the heater until a target resistance value is reached. Under a power control scheme, a certain amount of power is supplied to the heater arrangement and the power is monitored and adjusted to maintain the heater arrangement at a desired temperature. In a voltage control scheme, a certain voltage (e.g., 4 volts) can be continuously supplied to the heater arrangement and a program (e.g., algorithm) is used to monitor and maintain the voltage at a target value.

Figure 3:
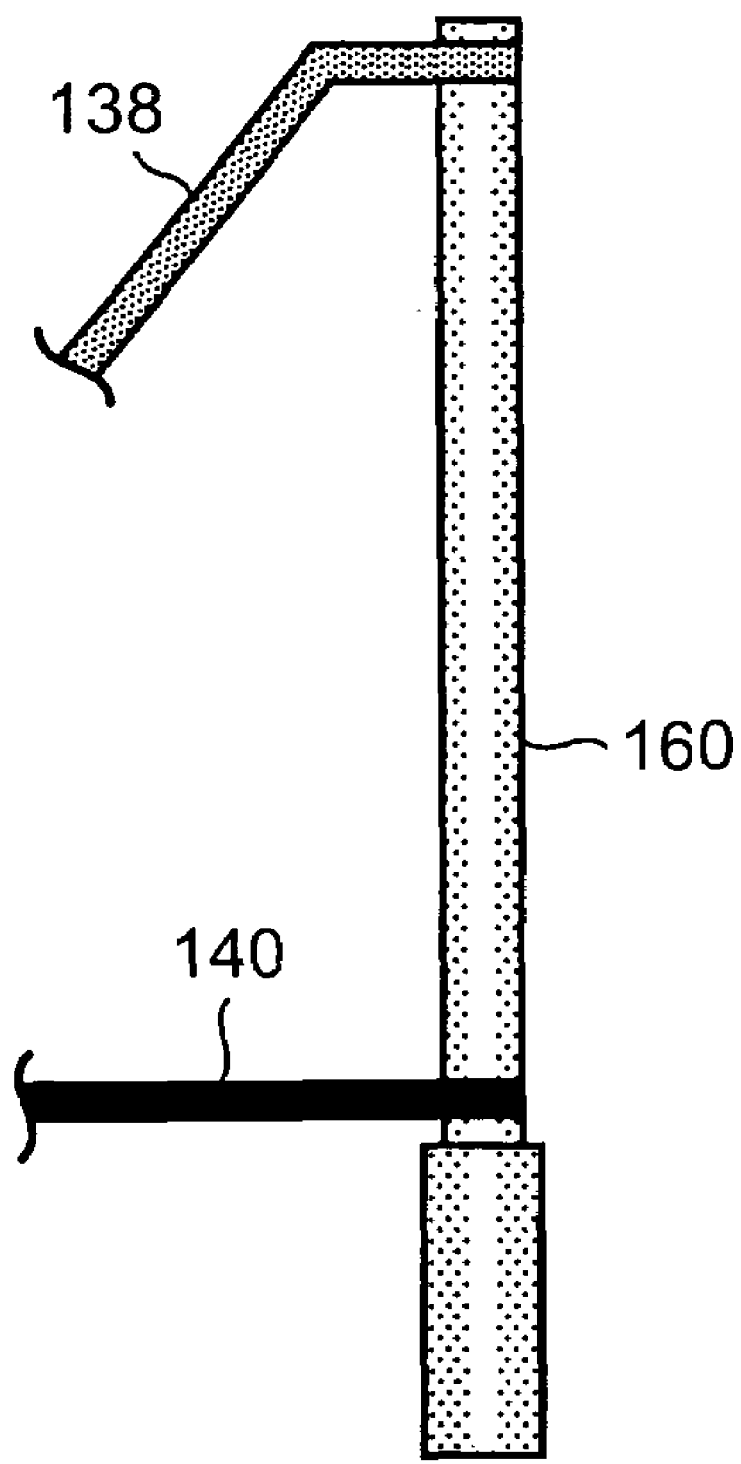
FIG. 3 illustrates an embodiment of the capillary passage including two electrodes.

The fluid supplied from the liquid source 106 is heated in the capillary passage to form a vapor during operation of the device 100. In a preferred embodiment shown in FIG. 3, the capillary passage 160 comprises metal tubing heated by passing an electrical current along a length of the capillary tube via a first electrode 138 and a second electrode 140. However, as described above, the capillary passage can have other alternative constructions, such as a monolithic or multi-layer construction, which include a heater such as a resistance heating material positioned to heat the fluid in the capillary passage. For example, the resistance heating material can be disposed inside of, or exterior to, the capillary passage. A plurality of separate heaters can be used to heat the flow passage.

The capillary passage 160 may comprise an electrically conductive tube provided with electrode 138 (e.g., a downstream electrode), and electrode 140 (e.g., an upstream electrode). Electrode 140 is preferably made of copper or a copper-based material, while electrode 138 is preferably made of a higher resistance material, such as stainless steel. In this embodiment, the capillary passage 160 has a controlled temperature profile construction, such as disclosed in commonly assigned U.S. Pat. No. 6,640,050, which is incorporated herein by reference in its entirety. In the controlled temperature profile capillary, the electrode 138 has an electrical resistance sufficient to cause the electrode 138 to be heated during operation of the device, thereby minimizing heat loss at the outlet end (e.g., downstream end) of the capillary passage.

The tube forming the capillary passage can be made entirely of stainless steel or any other suitable electrically conductive material(s). Alternatively, the tube can be made of a non-conductive or semi-conductive material incorporating a heater made from an electrically conductive material, such as palladium, platinum, iridium, etc. The region between the electrodes that are connected at spaced positions along the length of the tube or along a resistive heater defines a heated region along the capillary passage. A voltage applied between the two electrodes generates heat in the heated region of the capillary passage. The amount of heat generated is based on the resistivity of the material(s) making up the capillary tube or heater, and other parameters such as the cross-sectional area and length of the heated region. As fluid flows through the capillary passage into the heated region between the first and second electrodes, the fluid is heated and converted to a vapor of the carrier and nanoscale particles of the second component. The particles pass from the heated region of the capillary passage and exit from the outlet end. In some preferred embodiments, the particles are entrained in ambient air as the particles exit from the outlet. The entrainment in ambient air can disperse the nanoscale particles and, in the example of a hand held device, carry the nanoscale particles to the user. In a preferred embodiment, the MMAD of the nanoscale particles is less than about 100 nm, more preferably less than about 50 nm.

The temperature of the liquid in the capillary passage can be calculated based on the measured or calculated resistance of the heating element. For example, the temperature of the capillary passage heating element can be measured using infrared or optical pyrometry techniques. The heating element can be a portion of a metal tube, or alternatively a strip or coil of resistance heating material. Control electronics can be used to regulate the temperature of the capillary passage by monitoring the resistance of the heater.

Resistance control can be based on the simple principle that the resistance of the heater increases as its temperature increases. As power is applied to the heating element, its temperature increases because of resistive heating and the actual resistance of the heater also increases. When the power is turned off, the temperature of the heater decreases and correspondingly its resistance decreases. Thus, by monitoring a parameter of the heater (e.g., voltage across the heater using known current to calculate resistance) and controlling application of power, the control electronics can maintain the heater at a temperature that corresponds to a specified resistance target. One or more resistive elements could also be used to monitor temperature of the heated liquid in cases where a resistance heater is not used to heat the liquid in the capillary passage.

The resistance target is selected to correspond to a temperature that is sufficient to cause heat transfer to the liquid such that liquid is volatilized and expands out the open end of the capillary passage. The control electronics activate the heating, such as by applying pulsed energy to the heater for a duration of time, and after and/or during such duration, and determine the real time resistance of the heater using input from the measuring device. The temperature of the heater can be calculated using a software program designed to correlate measured resistance of the heater. In this embodiment, the resistance of the heater is calculated by measuring the voltage across a shunt resistor (not shown) in series with the heater (to determine current flowing to the heater) and measuring the voltage drop across the heater (to determine resistance based on the measured voltage and current flowing through the shunt resistor). To obtain a continuous measurement, a small amount of current can be continually passed through the shunt resistor and heater for purposes of making the resistance calculation. Pulses of higher current can be used to affect heating of the heater to the desired temperature.

If desired, the heater resistance can be derived from a measurement of current passing through the heater, or by other techniques used to obtain the same information. The control electronics determine whether or not to send an additional duration of energy based on the difference between desired resistance target for the heater and the actual resistance as determined by control electronics.

In a developmental model, the duration of power supplied to the heater was set at 1 millisecond. If the monitored resistance of the heater minus an adjustment value is less than the resistance target, another duration of energy is supplied to the heater. The adjustment value takes into account factors such as, for example, heat loss of the heater when not activated, the error of the measuring device, and the cyclic period of the controller and switching device. Because the resistance of the heater varies as a function of its temperature, resistance control can be used to achieve temperature control.

In embodiments, the capillary passage 160 can be constructed of two or more pieces of 32 gauge, 304 stainless steel tubing, though other sizes and compositions can be used. The downstream electrode can be a 3.5 mm length of 29 gauge tubing, while the upstream electrode may have any geometry that minimizes the resistance of the electrode, such as gold-plated copper pins.

The control electronics 120 can control the temperature of the capillary passage 160 by monitoring the resistance of the heater used to heat the capillary passage 160. In an embodiment, the control electronics 120 measures voltage and current in order to calculate the resistance across a length of the capillary passage 160. If the control electronics determines that the resultant resistance is below the target value, the control electronics turns power on for a selected period of time. The control electronics continues to repeat this process until the target resistance for the capillary passage 160 is reached. Likewise, if the control electronics determines that the resistance is higher than required for the temperature of the capillary passage 160, the control electronics turns off power for a selected period of time.

In this embodiment, the control electronics 120 may include any processor capable of controlling the resistance of the capillary passage 160 via the electrodes 138 and 140, such as a microchip PIC16F877, available from Microchip Technology Inc., located in Chandler, Ariz.

The pressure sensor 122 or switch 128 activates the fluid delivery assembly 110 to cause liquid 153 (e.g., a liquid nanoscale particle precursor material including a high volatility carrier and a drug) to flow from the liquid source 106 to the capillary passage 160 of the heater unit 130. The liquid is heated in the capillary passage 160 by the heater to a sufficiently high temperature to vaporize the liquid and form nanoscale particles.

In alternative embodiments, a pressurized air source can be used with the device to provide dilution air to mix with the aerosol. For example, the pressurized air source can be a compressed air source located within the device (not shown).

The control electronics 120 can perform various selected functions in the nanoscale particle generating device 100. For example, the control electronics 120 can control the temperature profile of the capillary passage 160 during operation of the device 100. The control electronics 120 can also control the output of the display 114. The display is preferably a liquid crystal display (LCD). The display can depict selected information pertaining to the condition or operation of the device 100. The control electronics can also control the operation of the inlet valve 156, discharge member 164 and/or outlet valve 158 during operation of the device 100; and monitor the condition of the battery unit 116 that provides electrical power to components of the device.

In the embodiment shown in FIG. 1, the battery unit 116 can be, for example, a rechargeable battery. The battery unit is preferably rechargeable via the charging jack 118. The battery unit provides power to components of the device (e.g., the control electronics 120, pressure sensor 122, etc.) and the master on/off switch.

The master on/off switch controls powering up and powering down of the device 100 during operation. The master on/off switch also activates the display 114. In an embodiment, the display provides information including, for example, the volume remaining within the liquid source 106, the status of the heater unit 130, and the status of charge remaining in the battery unit 116.

Liquid flows through the heated capillary passage 160 and exits as nanoscale particles. At the exit of the capillary passage 160, ambient air provided via the air passage 132 can disperse the nanoscale particles and, in the example of a hand-held device, carry the particles to the user.

Preferably, the particles have a MMAD less than about 500 nm, more preferably less than about 100 nm. However, in some other preferred embodiments, the particles can have a smaller particle size, such as an MMAD of less than about 50 nm, for example, less than about 25 nm. As described above, the nanoscale particle generating device can provide particles having a controlled particle size, including particles sized for the targeted delivery of drugs to the lung.

The device preferably generates particles in which 95% of the particles have a size in the range less than 500 nm. However, the nanoscale particles can contain particles smaller than 250 nm, such as, for example, less than 100 nm. For example, when the carrier is ethanol, the preferred particle size is less than 100 nm. Typically, the geometric standard deviation around the mass median aerodynamic diameter of the nanoscale particles is less than 2. Preferably, the geometric standard deviation is less than 1.9. More preferably, the geometric standard deviation is less than 1.8, 1.7, 1.6 or 1.5. The device preferably incorporates a processor chip for controlling the generation process.

The device can form nanoscale particles over a range of fluid flow rates dependent on the size of the capillary passage and the power used to vaporize the liquid.

As will be appreciated, the device is capable of controlled vaporization and nanoscale particle formation of drug formulations. The device can provide immediate delivery of aerosol to a patient, thereby not wasting lung capacity, which may be limited due to the health of the patient. The device can provide consistent delivery of controlled amounts of drug formulation to a patient. Also, the device can provide bulk volumes of nanoscale particles. A bulk volume is greater than 1 g, preferably greater than 10 g.

In a preferred embodiment, the collected amount of nanoscale particles can be at least about 75%, preferably about 75%-95%, of the metered dose of the liquid used to produce the nanoscale particles; the respirable fraction of the emitted dose can be at least 75%, preferably about 75%-95%, of the emitted dose; and the variation in the emitted dose can be less than about 5%.

In another embodiment having a heated capillary passage, the device can deliver a continuous stream of nanoscale particles. According to a preferred embodiment, the device can generate bulk volumes of nanoscale particles for use as medicaments, or as components in paints, scents, etc. As disclosed in commonly-assigned U.S. Provisional Patent Application No. 60/308,608, filed Jul. 31, 2001, the device may be operated intermittently, e.g., on demand, or continuously. For example, a nanoscale particle generation rate can be obtained on the order of 140 mg/hr. by flowing a 1% solution of budesonide in ethanol at 5 μL/sec. The bulk volume of budesonide nanoscale particles typically have a MMAD of 0.04 μm and a geometric standard deviation of 1.8. The nanoscale particles can be liquid or solid, depending on the equilibrium phase of the solute (e.g., second component).

EXAMPLES

Example 1

A solution of budesonide in ethanol was heated and vaporized in a heated capillary passage of a nanoscale particle generating device to produce dry, solid nanoscale particles of budesonide. The size distribution of particles was analyzed with a cascade impactor (MOUDI from MSP Corporation, located in Minneapolis, Minn.).

Tests were conducted using a 1% wt./vol. solution of budesonide in ethanol. The device included a 32 gauge, 17 mm long capillary passage. The particle generation time was 10 seconds. A 500 μL Hamilton syringe in a syringe pump was used as the fluid source to supply the liquid nanoscale particle precursor material to the capillary passage.

The particle size distribution determined with the cascade impactor indicated that the MMAD of the particles was very small. Visual inspection of the plates of the cascade impactor revealed that the deposited particles comprised a dry budesonide powder.

The cut diameters of the 10 stage MOUDI and the attached nano-MOUDI with an associated budesonide recovery for each stage, for replicate runs 1-3, are presented in Table 1. The data show that a major portion of the budesonide deposited in the nano-MOUDI stages. The data were fit to an assumed lognormal shape and the results are shown in Table 2. The average MMAD of the nanoscale particles for the three runs was 37 nm±4 nm, and the geometric standard deviation was 1.6±0.12. Clogging of the capillary passage of the device was not observed during these tests.

Example 2

Further tests were performed using a 1% wt./vol. solution of budesonide in ethanol as the liquid nanoscale particle precursor material. The device used in these tests included a 28 gauge capillary passage having a 25 mm length. A single particle size determination was made of the nanoscale particles produced using the solution. The particles had an average MMAD of about 0.06 μm with a geometric standard deviation of about 2.7.

Figure 4:
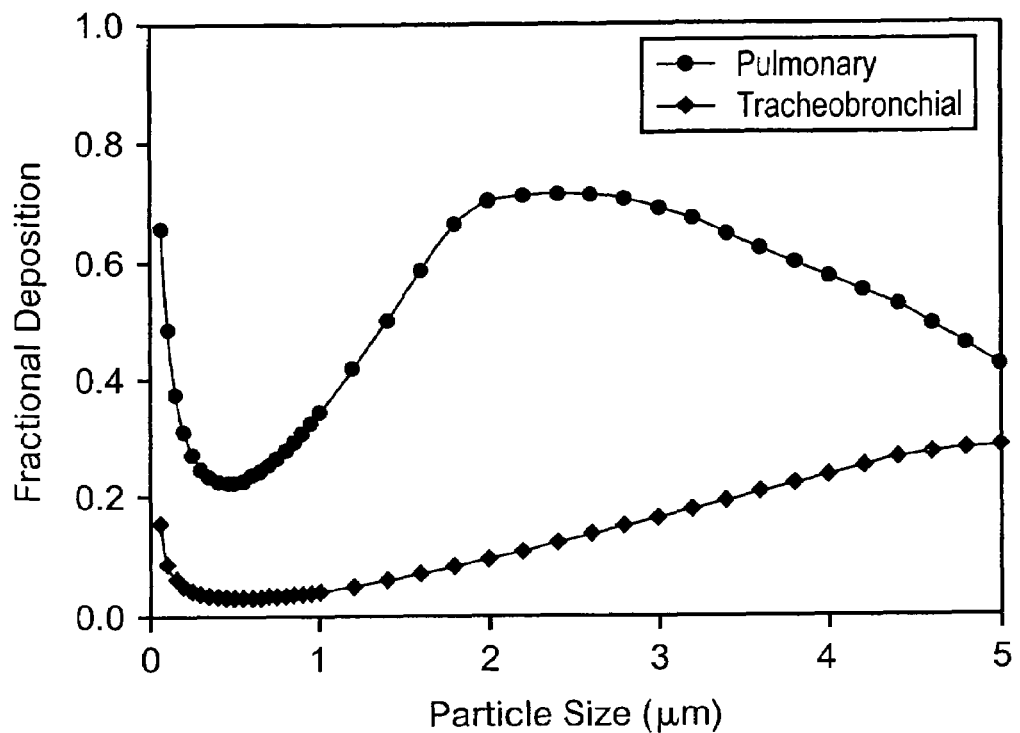
FIG. 4 shows theoretical plots of fractional deposition in the pulmonary and tracheobronchial regions of the lung versus particle size. The curve illustrated with diamonds shows tracheobronchial deposition and the curve illustrated with circles shows pulmonary deposition.

The extremely small particles that were produced by the device using the ethanol/budesonide solutions are highly efficient for delivering medicaments to the deep lung by diffusion. FIG. 4 shows theoretical plots of fractional lung deposition in the pulmonary and tracheobronchial regions versus particle size. As shown, the fractional particle distribution is greater in the pulmonary region than the tracheobronchial region over the depicted particle size range of up to 5 microns. FIG. 4 shows that lung deposition increases as the particle size decreases below about 500 nm (e.g., for the nanoscale particles that can be produced by aerosolizing a liquid nanoscale particle precursor material comprising a solute dissolved in a high volatility carrier).

TABLE 1

| Stage | Diameter of Particles Cut by Stage (μm) | Relative Recovery | | |
|---|---|---|---|---|
| | | Run 1 | Run 2 | Run 3 |
| Elbow Inlet | 18 | 0.162 | 0.222 | 0.086 |
| 1 | 10 | 0 | 0 | 0 |
| 2 | 5.6 | 0 | 0 | 0 |
| 3 | 3.2 | 0.279 | 0.173 | 0.067 |
| 4 | 1.8 | 0.593 | 0.398 | 0.283 |
| 5 | 1.0 | 1.27 | 1.03 | 0.834 |
| 6 | 0.56 | 1.20 | 0.983 | 0.824 |
| 7 | 0.32 | 1.23 | 1.16 | 1.05 |
| 8 | 0.18 | 1.01 | 0.891 | 0.883 |
| 9 | 0.1 | 1.85 | 1.93 | 2.08 |
| 10 | 0.056 | 2.40 | 2.67 | 2.80 |
| A-nano | 0.032 | 5.65 | 5.71 | 6.07 |
| B-nano | 0.018 | 6.13 | 5.72 | 6.64 |
| C-nano | 0.01 | 0.653 | 0.675 | 0.848 |
| Final Filter | 0 | 0 | 0 | 0 |

TABLE 2

| | Run 1 | Run 2 | Run 3 |
|---|---|---|---|
| MMAD (μm) | 0.034 | 0.035 | 0.041 |
| GSD | 1.52 | 1.54 | 1.74 |

Example 3

The effect of both the budesonide concentration in the liquid nanoscale particle precursor material and the fluid flow rate on the size of the particles produced was tested using 2.8% and 0.25% wt./vol. solutions of budesonide in ethanol at different flow rates.

Figure 5:
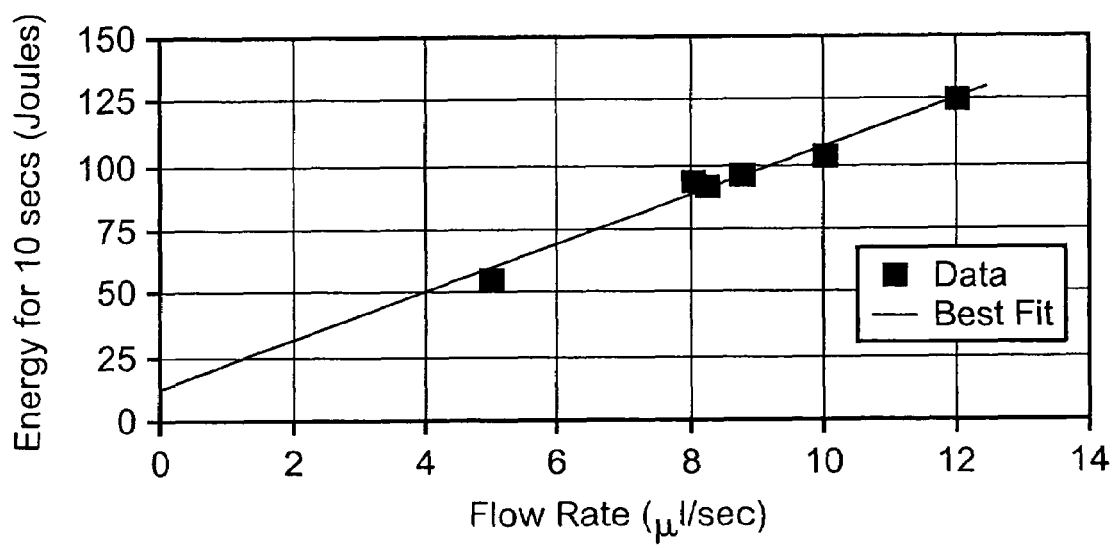
FIG. 5 shows the relationship between energy for 10 seconds (applied to the capillary sized passage) and fluid flow rate for a 2.8% budesonide in ethanol solution.

FIG. 5 shows the relationship between the energy applied to the capillary passage (for 10 seconds) for particle generation and the fluid flow rate for the 2.8% budesonide solution. The device performed automatic resistance control during operation. The control electronics of the device automatically adjusted the amount of energy delivered to the capillary heater to compensate for changes in the flow rate. FIG. 5 shows the linear relationship between the energy delivered to the heater and flow rate. FIG. 5 also shows that at zero fluid flow, the energy required to keep the heater at the target resistance (due to energy losses) is about 1.3 Watts.

Example 4

Three tests were conducted using a ten-stage MOUDI impactor (i.e., two additional final stages were added to the eight-stage device) to provide particle cuts down to 0.05 μm. Test results for a 2.8% wt./vol. solution of budesonide in ethanol at a fluid flow rate of 5 μL/sec are given in Table 3. Data were fitted to an assumed lognormal curve. Most of the collected particle mass was on the final filter, so the calculated MMAD values are indicative. The average MMAD values of the nanoscale particles for the three tests were approximately 0.01 μm.

TABLE 3

|  | Test 1 | Test 2 | Test 3 |
|---|---|---|---|
| MMAD (μm) | 0.02 | 0.01 | 0.01 |
| GSD | 6.2 | 5.6 | 5.8 |

Example 5

Figure 6:
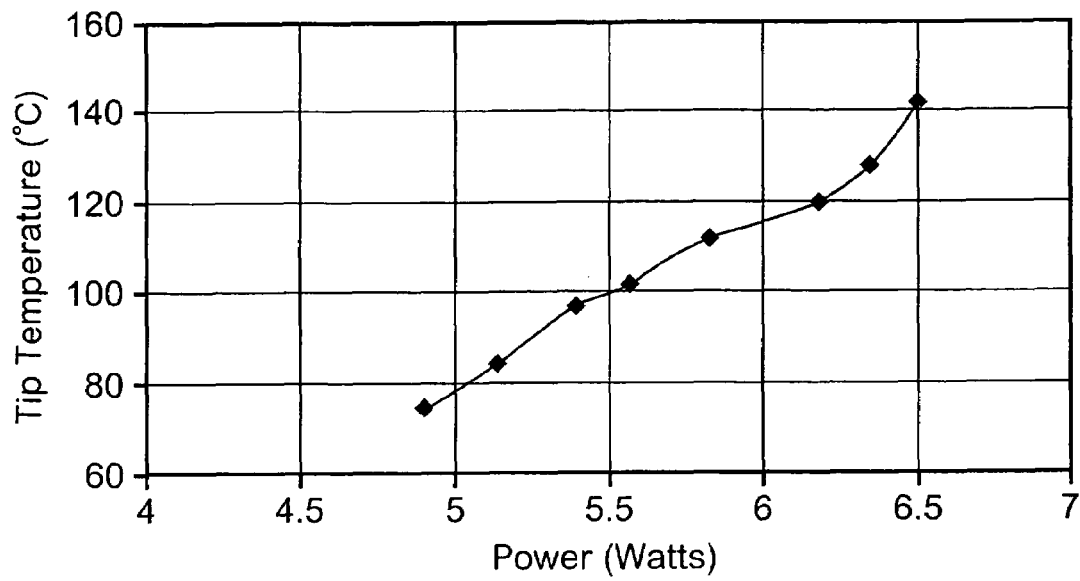
FIG. 6 illustrates the relationship between the tip temperature of a capillary sized passage and applied power.

The relationship between the tip (exit) temperature of the capillary passage of the device and the power applied to the capillary passage was evaluated. FIG. 6 shows the average tip temperature as a function of the applied power at a flow rate of 5 μL/sec. Ethanol has a boiling point of about 78.5° C. The optimal tune point of the capillary passage with respect to power was about 5.5 Watts, corresponding to a tip temperature of about 100° C. Accordingly, the tip temperature preferably is slightly above the boiling point of the carrier, for example, about 10-30° C. above the boiling point of the carrier. Using a high volatility carrier, the MMAD of the nanoscale particles has been shown to decrease with increasing capillary temperature.

Example 6

Further tests were performed to determine the effect of the budesonide concentration in the liquid nanoscale particle precursor material on the size of the nanoscale particles produced. Tests were performed using 0.2, 0.5, 1.0, and 2.0% wt./vol. solutions of budesonide in 100% ethanol. There was no indication of thermal breakdown of the budesonide. A syringe pump-(Harvard Apparatus, Holliston, Mass.) was used to meter the solutions at a pump rate of about 5 μL/sec. for a total run time of 10 seconds. The device included a 32 gauge stainless steel capillary tube with a heated length of 17 mm. Initial runs with a 10-stage MOUDI cascade impactor showed that 74% of the budesonide was deposited on the final filter, which was located downstream of a 0.05 μm final cut point. A nano-MOUDI cascade impactor, which is a three-stage, low-pressure impactor that attaches to the 10-stage MOUDI, was used for further work. The 10-stage MOUDI operates at a draw rate of 30 liters/min., while the nano-MOUDI draws 10 liters/min. of the sample from the tenth stage with the balance going to waste. Therefore, the quantity of budesonide collected on the nano-MOUDI stages was multiplied by a factor of three to adjust for the difference in sampling flow rate. The cut points of the nano-MOUDI stages are 0.032 μm, 0.018 μm and 0.010 μm, followed by a final filter. In addition to the MOUDI apparatus, particle size distribution measurements were made with a TSI scanning mobility particle sizer (TSI, Inc., St. Paul, Minn.). Scanning electron micrographs were taken of budesonide particles collected on a variety of substrates, including carbon planchets and aluminum foil impactor substrates.

Figure 7:
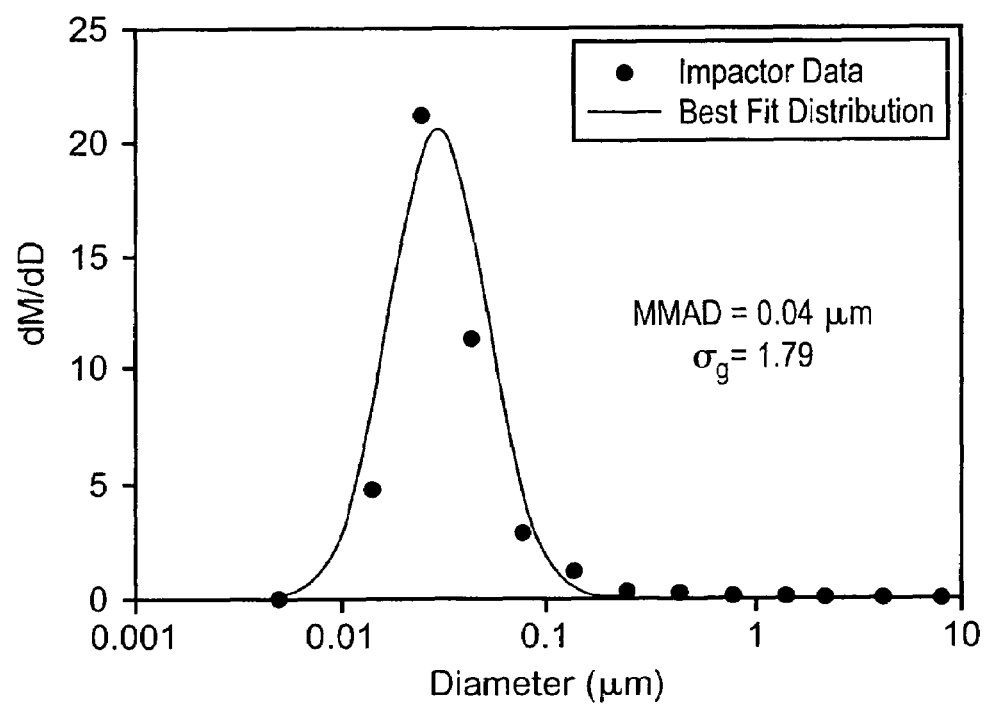
FIG. 7 illustrates a particle size distribution for a 1% budesonide in ethanol solution as measured by a 10 stage MOUDI impactor with an attached three stage nano-MOUDI.

The particle size distribution generated from a 1% budesonide solution in ethanol is shown in FIG. 7 as determined by the 10-stage MOUDI and nano-MOUDI cascade impactor. The data, which were fit to a log normal distribution, shows a MMAD of 0.04 μm and a geometric standard deviation of 1.79. The geometric standard deviation of a log normal distribution is determined by dividing the mass median particle diameter by the particle size at the 15.78 percent probability or by dividing the particle size at the 84.13 percent probability by the mass median particle diameter. The respirable fraction was calculated by taking the ratio of budesonide recovered on stages having cut points of less than 5.6 μm to the total amount of budesonide recovered. The respirable fraction for the 1% budesonide solution averaged 0.94.

Figure 8:
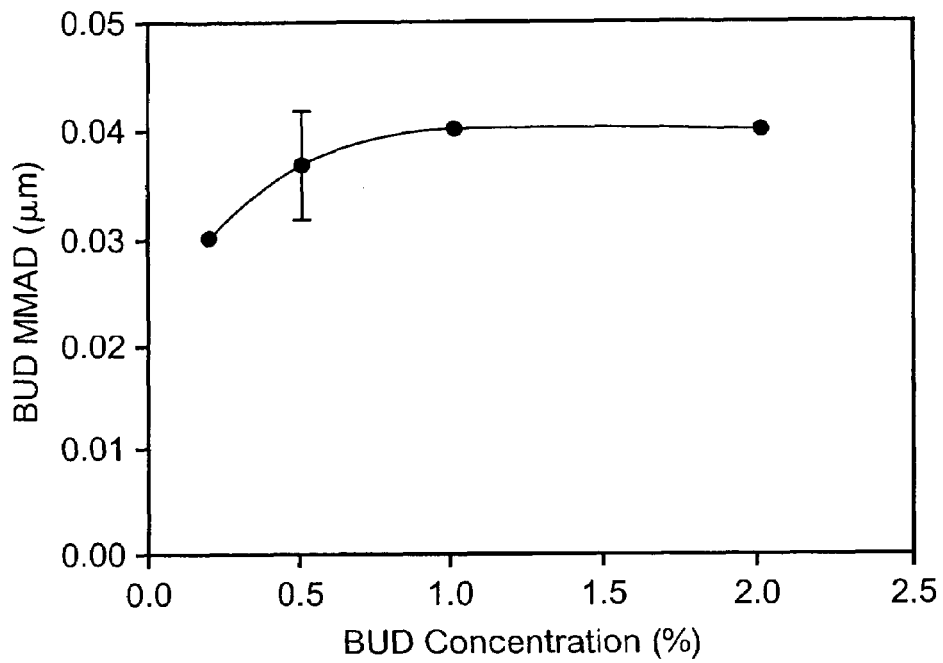
FIG. 8 shows the effect of budesonide concentration in ethanol on the MMAD of budesonide particles as measured by cascade impaction.

The effect of budesonide concentration on the particle MMAD as measured by cascade impaction is shown in FIG. 8. The MMAD increases from 0.03 μm for a 0.2% solution to 0.04 μm for 1% and 2% solutions.

Figure 9:
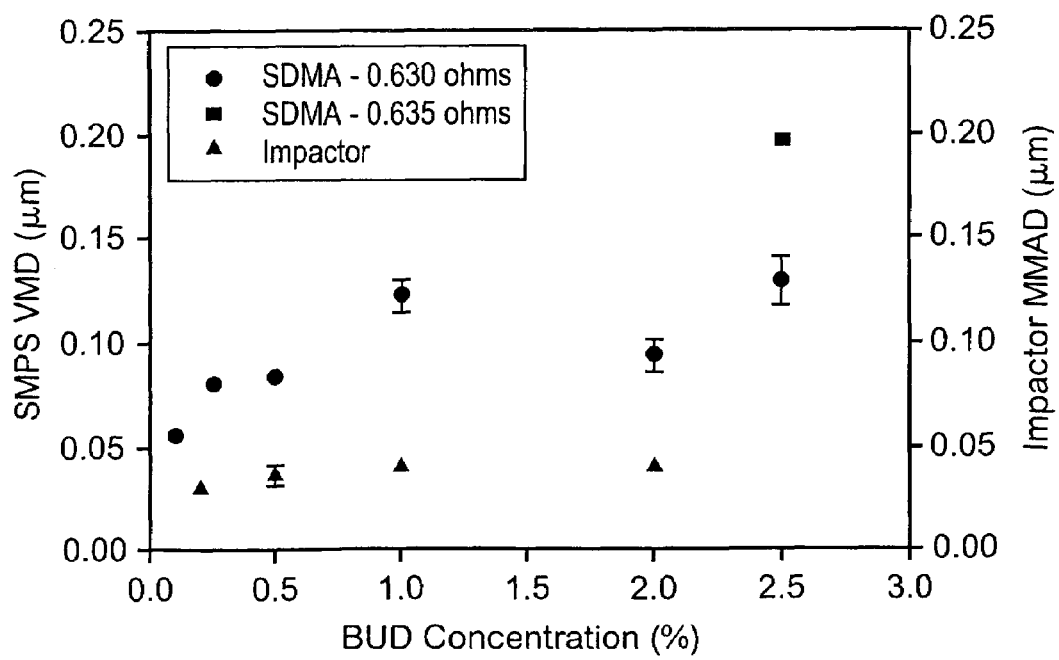
FIG. 9 shows the effect of budesonide concentration in ethanol on the volume mean diameters and MMAD of budesonide particles as measured by SMPS and cascade impaction, respectively.

The particle size distribution of nanoscale budesonide particles was also measured using a scanning mobility particle sizer (SMPS). The volume mean diameters calculated using SMPS as well as the MMADs from the cascade impactor are shown in FIG. 9 as a function of budesonide concentration in ethanol. The circles represent the SMPS data corresponding to a resistance target of 0.630 ohms, and the square represents the SMPS data corresponding to a resistance target of 0.635 ohms. The SMPS measured diameter increased significantly by increasing the temperature of the capillary passage for the 2.5% solution (i.e., by raising the resistance target from 0.630 to 0.635 ohms). Without wishing to be bound by theory, it is believed that the higher budesonide concentrations require an increase in the applied energy to achieve a desired particle size distribution and/or yield.

Figure 10:
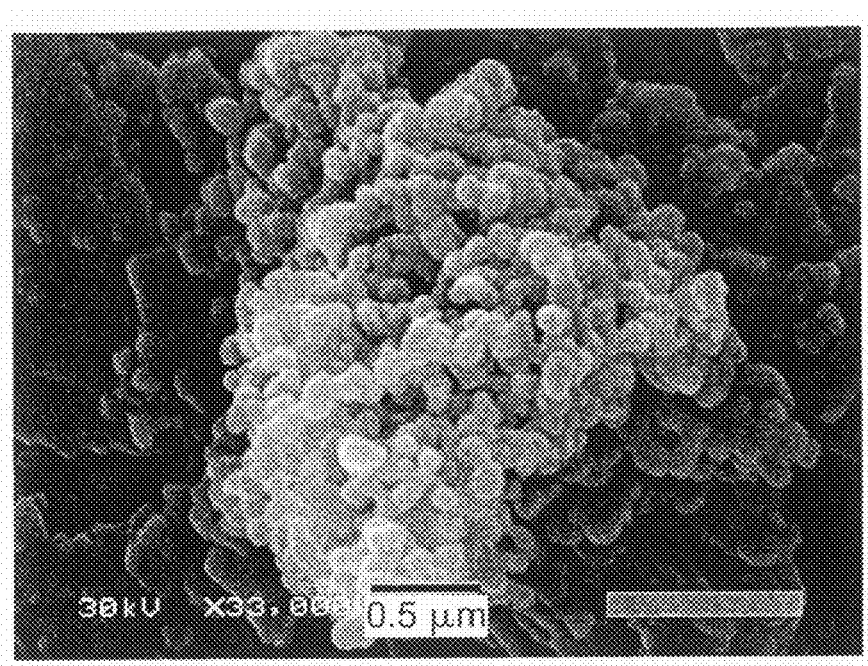
FIG. 10 shows an SEM micrograph of budesonide particles formed from a 1% budesonide in ethanol solution and collected from the tenth stage of a 10-stage MOUDI cascade impactor.
Figure 11:
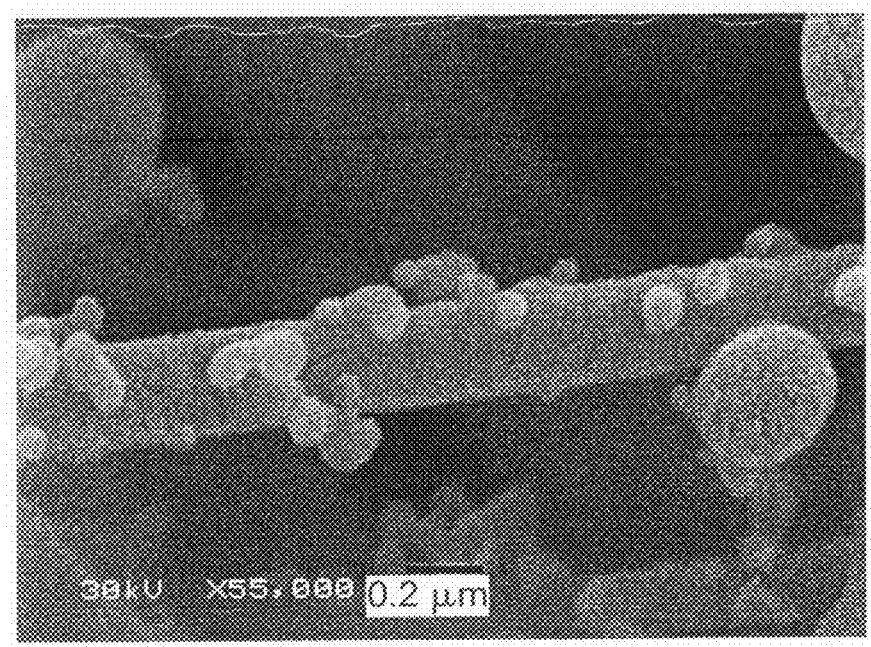
FIG. 11 shows an SEM micrograph of budesonide particles formed from a 1% budesonide in ethanol solution and collected on a glass fiber filter.

FIGS. 10 and 11 show SEM images of budesonide particles generated from a 1% solution of budesonide in ethanol. An SEM micrograph of budesonide particles collected from stage 10 of a 10 stage MOUDI cascade impactor is shown in FIG. 10. The particles, which have agglomerated after collection at the impactor, have an average diameter consistent with the 0.05 μm cut point that is upstream of the tenth stage.

FIG. 11 shows an SEM image of budesonide particles collected on a the glass fibers of a glass fiber filter. The budesonide particles are nearly spherical (or ovoid) in shape and have diameters as small as 0.05 μm.

The above-described test results demonstrate that the nanoscale particle generating device can be used to generate budesonide particles with up to 100% recoveries, no observable degradation, and nanoscale particle sizes for inhalation, using a high volatility carrier such as ethanol. In addition, the test results demonstrate that the particle size can be controlled by varying the medicament concentration and/or fluid flow rate of the liquid nanoscale particle precursor material.

Example 7

Figure 12:
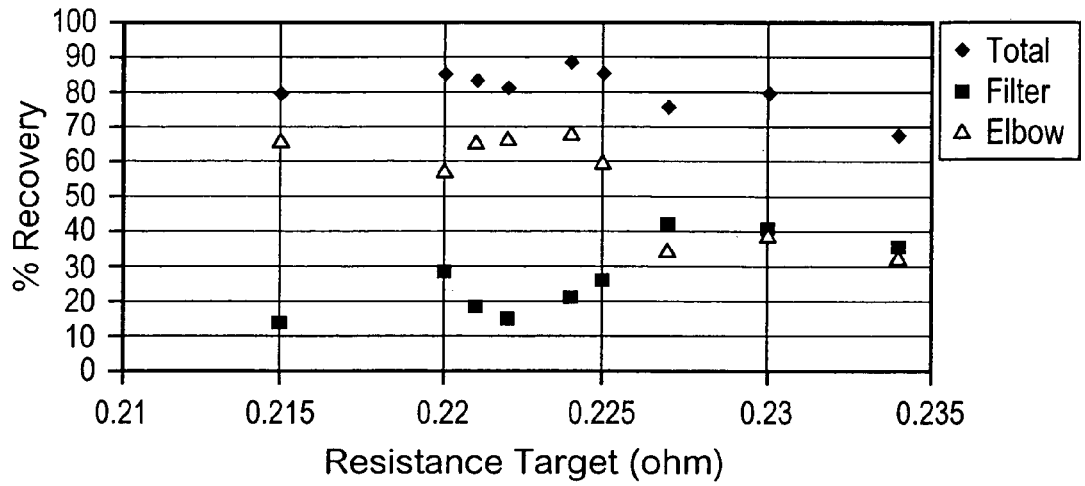
FIG. 12 illustrates the % recovery of albuterol sulfate for a 1% solution of albuterol sulfate in water at a fluid flow rate of 5 µL/sec.

Further tests were conducted to demonstrate that the nanoscale particle generating device is also capable of generating particles using water as the high volatility carrier. FIG. 12 shows the percent recovery of albuterol sulfate for a 1 wt. % solution of albuterol sulfate in water at a solution flow rate of 5 μL/sec using a 26 gauge capillary passage having a length of 21 mm. The results indicate that by increasing the resistance target to about 0.23 ohms, about 40% of the albuterol sulfate was recovered on the filter and about 40% was deposited in the elbow.

Example 8

Figure 13:
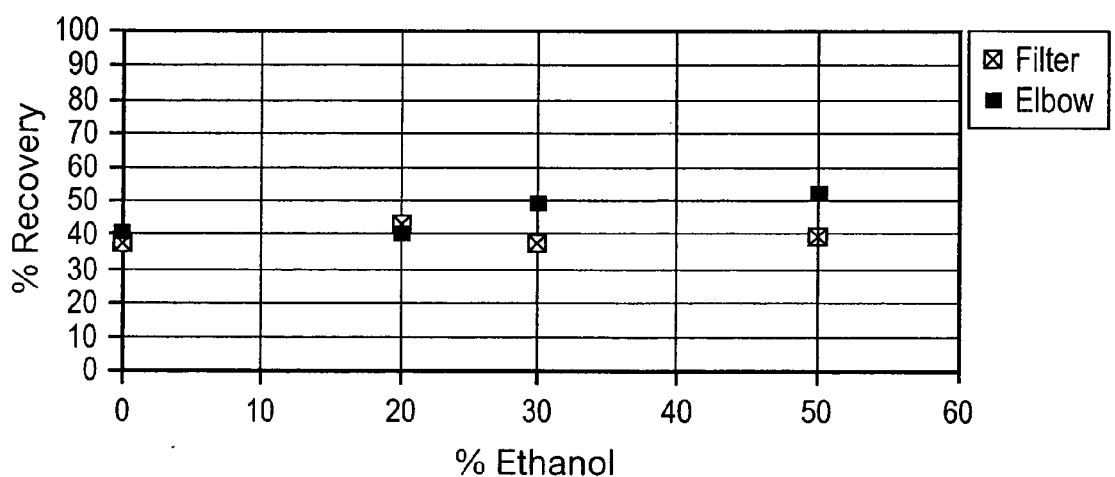
FIG. 13 illustrates the % recovery of albuterol for albuterol solutions containing varying percentages of ethanol and water.

Tests were also conducted to determine the effect on the albuterol particle size distribution and MMAD when ethanol is added to the albuterol/water solution used in Example 8. That is, two high volatility carriers, water and ethanol, were used as the carrier. FIG. 13 shows the recovery of albuterol in the albuterol/ethanol/water system at different volume percentages of ethanol in the carrier ranging from 0 volume % ethanol (i.e., 100 volume % water) to 50 volume % ethanol (i.e., 50 volume % water). Increasing the volume percentage of ethanol (decreasing the volume percentage of water) in the carrier increased slightly the amount of albuterol recovered on the elbow, while the amount of albuterol recovered on the filter remained approximately constant.

Figure 14:
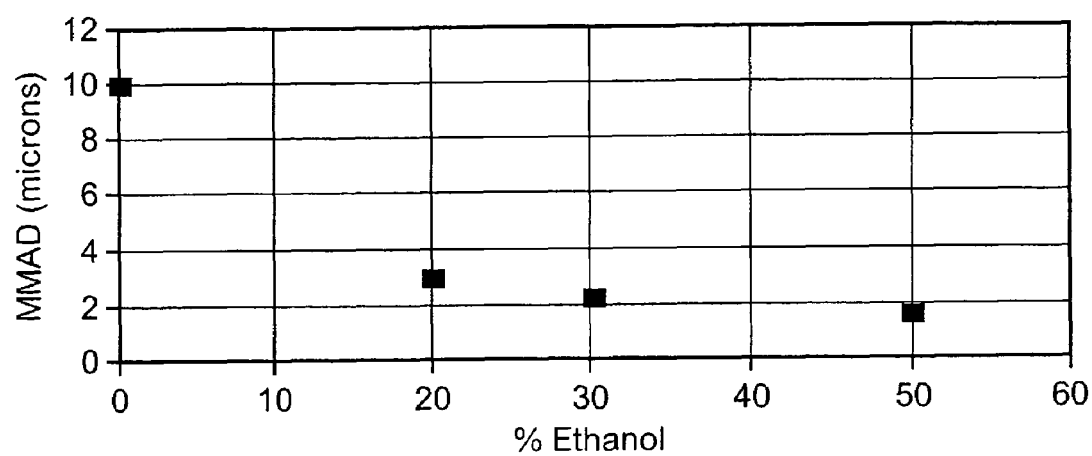
FIG. 14 illustrates the MMAD of albuterol particles versus volume % ethanol in water for albuterol solutions containing varying volume percentages of ethanol and water.

The effect of varying the percentage of ethanol in the carrier on the albuterol MMAD for up to 50 volume % ethanol additions was also investigated. FIG. 14 shows that increasing the percentage of ethanol in the carrier from 0 to 50% decreased the MMAD of albuterol particles by more than a factor of 5.

Nanoscale albuterol particles produced using a carrier containing varying percentages of ethanol in water as described above were visually analyzed and determined to be dry particles.

Example 9

Figure 15:
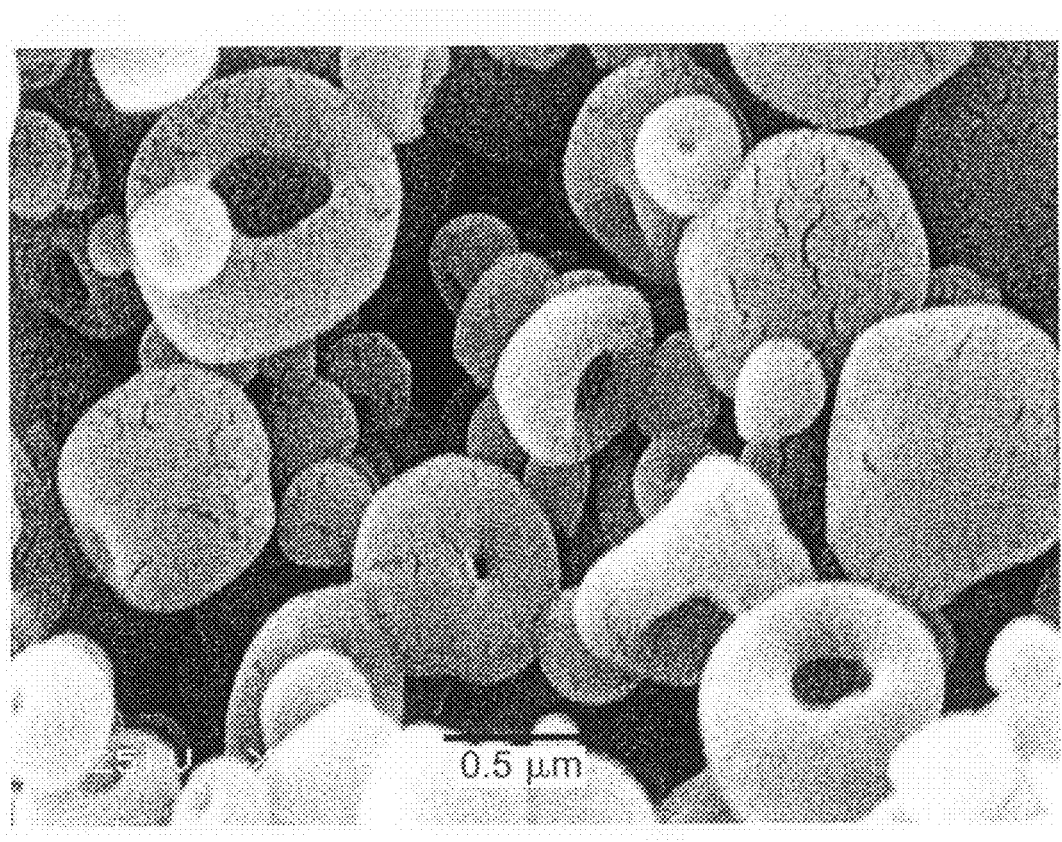
FIG. 15 shows an SEM micrograph of insulin particles. The particles were formed by aerosolizing a 1 wt. % insulin solution in 20% water/80% ethanol mixture.

A solution of 1% insulin in a 20% water, 80% ethanol solution was heated and vaporized in a heated capillary passage of a nanoscale particle generating device. The resulting particles were admixed with air to form a dry stream of insulin particles. An SEM micrograph of the aerosolized human insulin particles is shown in FIG. 15.

The Example test results demonstrate that nanoscale particles can be produced from liquid nanoscale particle precursor materials containing a selected aerosol-forming component and one or more high volatility carriers. The nanoscale particles can be produced using various aerosol-forming components, such as albuterol and budesonide, and one or more high volatility carriers. In a preferred embodiment, the particles produced from the liquid nanoscale particle precursor material are substantially dry particles of the component (i.e., the particles contain substantially no liquid resulting from conversion of the high volatility carrier to an aerosol).

Furthermore, the test results demonstrate that nanoscale particles can be produced from liquid nanoscale particle precursor materials containing a selected aerosol-forming component and a carrier, which contains at least one high volatility carrier, such as ethanol, or a mixture of ethanol and water. Alternatively, the high volatility carrier can be water alone. Nanoscale particles produced using a water-containing carrier preferably are dry particles of the aerosol-forming component.

Example 10

A 1% solution of budesonide in acetone was heated and vaporized in a heated capillary passage of a nanoscale particle generating device. A solution flow rate of 5 µL/sec, and a 0.15 mm inner diameter capillary passage having a length of 35 mm were used. Data from a 10-stage MOUDI, which were fit to a log normal distribution, show a MMAD of 0.02 µm and a geometric standard deviation of 3.02.

Using a liquid nanoscale particle precursor material comprising at least one high volatility carrier and at least one other component can provide the capability of delivering dry nanoscale powders.

The particles produced from the liquid nanoscale particle precursor materials using high volatility carriers can be used in a variety of applications including, for example, the controlled generation of nanoscale particles of medicaments for targeted delivery to the lungs via inhalation; the preparation of finely divided medications; the controlled (continuous or non-continuous) generation of fine particles for industrial uses; and the production of jets of fine particles for coating objects.

Methods for collecting the nanoscale particles directly from the aerosol stream include filtration, condensation and diffusional capture. The filtration method can involve passing the aerosol of nanoscale particles through a filter to physically trap the nanoscale particles. The filtration method can yield a bulk volume of material. The condensation method involves passing the aerosol through an enclosed volume containing the saturated vapor of a suitable liquid that condenses on the nanoscale particles. Conventional centrifugal separation and sedimentation techniques can be used to remove the liquid-laden nanoscale particles from the air stream. According to a preferred embodiment, the nanoscale particles can be collected directly from the aerosol stream and incorporated into a liquid suspension. Diffusional capture methods take advantage of the high diffusivity of the nanoscale particles and can be used to form a liquid suspension of the nanoscale particles directly from the aerosol stream. Techniques that use diffusional capture principles include falling films, liquid sprays, thermophoretic capture and electrostatic capture. For example, the thermophoretic and electrostatic separation of aerosol particles from a gas stream is disclosed in U.S. Pat. Nos. 4,572,007 and 6,096,118, respectively.

Controlled release composite particles of micron or nanoscale size containing at least one medicament and at least one control release agent can be prepared by vaporizing a formulation containing the medicament and control release agent to form an aerosol comprising solid composite control release particles of the medicament and agent. The control release agent can be at least one biocompatible polymer, sugar, aliphatic acid or the like. The formulation can be a suspension containing medicament particles or solution in which the medicament is at least partially dissolved. The solution is preferably an organic liquid such as ethanol, methanol, ethyl acetate, acetone, methyl ethylene, methylene chloride, chloroform, DMSO, mixtures thereof and optional aerosol particle size controlling agents such as water. For example, the solution can contain a control release agent in the form of a biodegradable polymer such as polylactic acid (e.g., up to 5 wt. %), a medicament such as budesonide in an amount (e.g., up to 5 wt. %) and acetone in which the budesonide and polylactic acid are dissolved. After vaporization and aerosolization of the solution using a capillary aerosol generator (i.e., capillary heater) as described herein, composite particles of budesonide and polylactic acid can be collected.

As a result of valorization and aerosolization using the capillary heater, controlled release particles can be produced with desired particle sizes such as micron sized particles (e.g., 0.5 to 10 µm) or nanosized particles (e.g., less than 1 µm, preferably less than 500 nm such as 1 to 100 nm or 100 to 500 nm). The particles are preferably solid particles consisting of the medicament and the control release agent, e.g., budesonide and polylactic acid. The particles can comprise a homogeneous mixture of medicament and control release agent or a core and shell structure of medicament surrounded by the control release agent. The relative amounts of medicament and agent (e.g., 1 to 99 wt. % medicament) can be adjusted to achieve a desired release rate of the medicament. For example, if the medicament is readily released when administered, the agent can be selected and incorporated in an amount to retard the release rate of the medicament. Conversely, if the medicament is not readily released when administered, the agent can be selected and incorporated in an amount which promotes the desired release rate of the medicament.

The medicament and organic solvent can be selected to achieve vaporization of the solution containing the medicament and release agent at temperatures preferably below 100° C., more preferably below 90° C., e.g., at temperatures from about 30 to 80° C. Because the heated capillary can generate controlled release aerosol particles at temperatures below 100° C., a larger selection of potential drug compounds can be incorporated in the controlled release particles. Thus, commercial production of controlled release particles having desired particle sizes and release rates can be achieved using the heated capillary in a batch or continuous manner. For example, a solution of medicament and agent could be fed to one or more heated capillaries to mass produce controlled release particles at a desired rate, e.g., hundreds of grams of particles per day.

The composite controlled release particles can be administered by various techniques. For example, the composite particles can be inhaled as an aerosol produced by the capillary aerosol generator in which case the solution or suspension containing the additive and medicament will include an FDA approved carrier. Alternatively, collected composite particles can be formed into tablets or capsules for oral administration or injected as a suspension into the bloodstream of a subject such as a human patient via intravenous or intramuscular injection using a syringe or administered topically as a cream, lotion, patch, etc. Another technique involves aerosolizing a suspension of the composite particles via a nebulizer or propellant driven metered dose inhaler device or using a capillary aerosol generator which vaporizes a suspension of the particles to form an aerosol of the particles.

The above-described exemplary modes of carrying out the invention are not intended to be limiting. It will be apparent to those of ordinary skill in the art that modifications thereto can be made without departure from the spirit and scope of the invention as set forth in the accompanying claims. For instance, while a heated capillary tube has been described as the preferred construction of the capillary passage, the capillary passage can comprise one or more channels in a laminate having a heater arranged along the channel(s), multiple capillary tube arrangements, a passage having a heater located inside the passage, coaxial arrangements including an annular channel for fluid flow, or the like.

What is claimed is:

1. A method of generating nanoscale particles, comprising:
   (a) supplying a liquid nanoscale particle precursor material comprising a high volatility carrier having a boiling point of 100° C. or less and an additional component from a liquid source to a flow passage;
   (b) heating the liquid nanoscale particle precursor material in a heated portion of the flow passage; and
   (c) vaporizing the high volatility carrier to produce an aerosol stream of nanoscale particles that exit an open end of the flow passage, wherein the nanoscale particles have a mass median aerodynamic diameter of less than about 50 nm.

2. The method of claim 1, wherein the high volatility carrier is selected from the group consisting of ethanol, water, acetone, ethyl acetate, hexanes, isopropanol, butanol and mixtures thereof.

3. The method of claim 1, wherein the high volatility carrier comprises ethanol.

4. The method of claim 1, wherein the high volatility carrier comprises ethanol and the liquid nanoscale particle precursor material comprises at least about 1 weight % budesonide.

5. The method of claim 1, wherein the high volatility carrier comprises ethanol and the additional component is selected from the group consisting of albuterol and budesonide.

6. The method of claim 1, wherein the high volatility carrier comprises an ethanol-water mixture.

7. The method of claim 1, wherein the high volatility carrier consists essentially of 0-100 volume % water and about 100-0 volume % ethanol.

8. The method of claim 1, wherein the additional component comprises a medicament.

9. The method of claim 1, wherein the additional component comprises a medicament selected from the group consisting of antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesic and stimulants.

10. The method of claim 1, wherein the additional component is selected from the group consisting of albuterol and budesonide.

11. The method of claim 1, further comprising dissolving the additional component in the carrier.

12. The method of claim 1, wherein the liquid nanoscale particle precursor material is propellant free.

13. The method of claim 1, wherein the nanoscale particles consist essentially of the additional component.

14. The method of claim 1, wherein the nanoscale particles consist essentially of substantially dry solid particles.

15. The method of claim 1, wherein the nanoscale particles have a mass median aerodynamic diameter of less than 25 nm.

16. The method of claim 1, wherein the nanoscale particles consist essentially of the medicament.

17. The method of claim 1, wherein the nanoscale particles comprise magnetic nanoscale particles.

18. The method of claim 1, wherein the nanoscale particles comprise nanoscale particles having a ferritic structure.

19. The method of claim 1, wherein the nanoscale particles comprise abrasive nanoscale particles.

20. The method of claim 1, wherein the nanoscale particles comprise nanoscale particles of an element selected from the group consisting of cobalt, nickel, bismuth and silicon.

21. The method of claim 1, wherein the nanoscale particles comprise nanoscale particles of a metal, metal oxide and or alloy.

22. The method of claim 21, wherein the nanoscale particles comprise magnetic nanoscale particles.

23. The method of claim 21, wherein the nanoscale particles have a ferritic structure.

24. The method of claim 21, wherein the nanoscale particles comprise abrasive nanoscale particles.

25. The method of claim 21, wherein the nanoscale particles consist essentially of an element selected from the group consisting of cobalt, nickel, bismuth and silicon.

26. The method of claim 1, wherein the flow passage is a capillary sized flow passage.

27. The method of claim 1, further comprising:
   supplying a predetermined volume of the liquid nanoscale particle precursor material into the heated portion of the flow passage; and
   heating the predetermined volume of the liquid nano scale particle precursor material to produce the nanoscale particles.

28. The method of claim 1, wherein (a)-(c) are performed using a nanoscale particle generating device comprising a mouthpiece, the method further comprising:
   supplying a predetermined volume of the liquid nanoscale particle precursor material into the heated portion of the flow passage; and
   delivering the aerosol to the user through the mouthpiece.

29. The method of claim 1, comprising producing the nanoscale particles continuously.

30. The method of claim 1, further comprising:
performing (a)-(c) using a first fluid delivery assembly attached to a nanoscale particle generating device comprising the flow passage;
removing the first fluid delivery assembly from the nanoscale particle generating device;
attaching a second fluid delivery assembly to the nanoscale particle generating device; and
repeating (a)-(c) using the second fluid delivery assembly.

31. The method of claim 30, wherein the first fluid delivery assembly supplies a first liquid nanoscale particle precursor material, and the second fluid delivery assembly supplies a second liquid nanoscale particle precursor material different from the first liquid nanoscale particle precursor material.

32. The method of claim 30, comprising producing a first aerosol containing aerosol nanoscale particles having a first mass median aerodynamic diameter with the first fluid delivery assembly, and producing a second aerosol containing nanoscale particles having a second mass median aerodynamic diameter different from the first mass median aerodynamic diameter with the second fluid delivery assembly,
wherein the nanoscale particles in the first aerosol, the second aerosol, or both the first aerosol and the second aerosol, have a mass median aerodynamic diameter of less than about 5 nm.

33. The method of claim 1, further comprising collecting the nanoscale particles directly from the aerosol stream using filtration, condensation or diffusional capture.

34. The method of claim 1, further comprising forming a liquid suspension of the nanoscale particles directly from the aerosol stream.

35. The method of claim 1, comprising heating the liquid nanoscale particle precursor material to a temperature of at least 2 times the boiling point of the high volatility carrier.

36. The method of claim 1, comprising heating the liquid nanoscale particle precursor material to a temperature of at least 3.5 times the boiling point of the high volatility carrier.

37. A method of generating nanoscale particles, comprising:
(a) supplying a liquid nanoscale particle precursor material comprising a high volatility carrier having a boiling point of 100° C. or less and a medicament selected from the group consisting of albuterol and budesonide from a liquid source to a flow passage; and
(b) heating the liquid nanoscale particle precursor material in a heated portion of the flow passage to produce nanoscale particles, wherein the nanoscale particles have a mass median aerodynamic diameter of less than about 50 nm.

38. The method of claim 37, wherein the high volatility carrier is selected from the group consisting of ethanol, water, acetone, ethyl acetate, hexanes, isopropanol, butanol and mixtures thereof.

39. The method of claim 37, wherein the high volatility carrier consists essentially of 0-100 volume % water and about 100-0 volume % ethanol.

40. The method of claim 37, wherein the high volatility carrier Comprises ethanol.

41. The method of claim 37, wherein the nanoscale particles have a mass median aerodynamic diameter of less than 25 nm.

42. The method of claim 37, wherein the nanoscale particles consist essentially of the medicament.

43. A method of generating controlled release composite particles, comprising:
(a) supplying a liquid composite particle precursor material comprising a carrier, at least one medicament and at least one control release agent from a liquid source to a flow passage;
(b) heating the liquid composite particle precursor material in a heated portion of the flow passage; and
(c) vaporizing the carrier to produce an aerosol stream of composite particles that exit an open end of the flow passage, wherein the composite particles have a mass median aerodynamic diameter of less than about 50 nm.

44. The method of claim 43, wherein the carrier has a boiling point of 100° C. or less.

45. The method of claim 43, wherein the carrier comprises ethanol, methanol, ethyl acetate, acetone, methyl ethylene, methylene chloride, chloroform, DMSO, or mixture thereof.

46. The method of claim 43, wherein the a carrier further comprises an aerosol particle size controlling agent.

47. The method of claim 43, wherein the control release agent comprises a biocompatible polymer, sugar, aliphatic acid or mixture thereof.

48. The method of claim 43, wherein the medicament is selected from the group consisting of antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesic and stimulants.

49. The method of claim 43, wherein the medicament consists essentially of budesonide and the control release agent consists essentially of PLA.

50. The method of claim 43, further comprising dissolving the medicament in the carrier.

51. The method of claim 43, wherein the liquid composite particle precursor material is propellant free.

52. The method of claim 43, comprising forming the composite particles consisting essentially of the medicament and the control release agent.

53. The method of claim 43, comprising forming the composite particles consisting essentially of substantially dry solid particles.

54. The method of claim 43, wherein the flow passage is a capillary sized flow passage.

55. The method of claim 43, comprising producing the composite particles continuously.

56. The method of claim 43, wherein the carrier comprises the liquid composite particle precursor material comprising up to 5 weight % medicament and up to 5 weight % control release agent.

* * * * *